(12) United States Patent
Bristow

(10) Patent No.: US 9,334,241 B2
(45) Date of Patent: May 10, 2016

(54) PROCESS FOR THE PREPARATION OF N-SUBSTITUTED PYRAZOLE COMPOUNDS

(75) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/345,135

(22) PCT Filed: Sep. 12, 2012

(86) PCT No.: PCT/CN2012/081295
§ 371 (c)(1),
(2), (4) Date: Mar. 14, 2014

(87) PCT Pub. No.: WO2013/037291
PCT Pub. Date: Mar. 21, 2013

(65) Prior Publication Data
US 2014/0350267 A1    Nov. 27, 2014

(30) Foreign Application Priority Data
Sep. 14, 2011   (BR) ..................................... 1104747

(51) Int. Cl.
*C07D 231/44*   (2006.01)
*C07D 231/18*   (2006.01)
*A01N 43/56*   (2006.01)

(52) U.S. Cl.
CPC ............. *C07D 231/44* (2013.01); *A01N 43/56* (2013.01); *C07D 231/18* (2013.01)

(58) Field of Classification Search
CPC ........................... C07D 231/44; C07D 231/18
See application file for complete search history.

(56) References Cited

U.S. PATENT DOCUMENTS

| 5,580,843 | A | 12/1996 | Stetter et al. |
| RE37,495 | E | 1/2002 | Stetter et al. |
| 2007/0116550 | A1 | 5/2007 | Nakamura et al. |
| 2011/0034530 | A1 | 2/2011 | Yang et al. |
| 2012/0215008 | A1 | 8/2012 | Korte et al. |

FOREIGN PATENT DOCUMENTS

| CN | 1107842 A | 9/1995 |
| CN | 101168529 A | 4/2008 |
| CN | 101250158 A | 8/2008 |
| CN | 101544607 A | 9/2009 |
| CN | 101554607 A | 10/2009 |
| CN | 101628895 A | 1/2010 |
| CN | 101723898 A | 6/2010 |
| CN | 101955460 A | 1/2011 |
| CN | 101970413 A | 2/2011 |
| WO | 2009077853 A1 | 6/2009 |
| WO | 2011051284 A | 5/2011 |
| WO | 2011089616 A1 | 7/2011 |

OTHER PUBLICATIONS

PCT/CN2012/081295—International Search Report, dated Dec. 20, 2012, 7 pgs.

*Primary Examiner* — Samantha Shterengarts
(74) *Attorney, Agent, or Firm* — Dickinson Wright PLLC

(57) ABSTRACT

A process for the preparation of a compound of formula I:

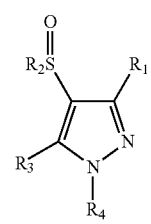

(I)

wherein,
$R_1$ represents hydrogen, cyano, nitro, halogen, or acyl;
$R_2$ represents aryl, alkenyl, alkynyl, halogen substituted alkyl, halogen substituted alkenyl, or halogen substituted alkynyl;
$R_3$ represents hydrogen or $NR_6R_7$ wherein $R_6$ and $R_7$ each independently represent hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with, the N atom attached form a heterocycle; and
$R_4$ represents hydrogen, alkyl, aryl, or heteroaryl;
the process including oxidizing a compound of formula II:

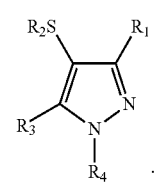

(II)

23 Claims, No Drawings

PROCESS FOR THE PREPARATION OF N-SUBSTITUTED PYRAZOLE COMPOUNDS

This application is a 371 of PCT/CN2012/081295, filed 12 Sep. 2012, which claims the benefit of Brazilian Patent Application PI1104747-0, filed 14 Sep. 2011, the entire contents of each of which are incorporated herein by reference for all purposes.

FIELD OF THE INVENTION

The present invention relates to a process for the preparation of phenyl pyrazole compounds, particularly 5-amino-3-cyano-1-(2,6-dichloro-4-trifluoromethylphenyl)-4-trifluoromethyl sulphinyl pyrazoles. Such compounds are known to exhibit insecticidal properties.

BACKGROUND OF THE INVENTION

It has been reported in EP 0 295 117 A that N-substituted pyrazole derivatives as defined by the general formula I:

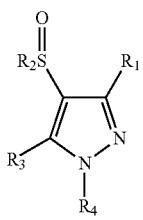

(I)

wherein,
$R_1$ represents hydrogen, cyano, nitro, halogen, or acyl, such as $C_1$-$C_4$ acyl;
$R_2$ represents alkyl, alkenyl, alkynyl, halogen substituted alkyl, halogen substituted alkenyl, or halogen substituted alkynyl;
$R_3$ represents hydrogen or $NR_6R_7$ wherein $R_6$ and $R_7$ each independently represent hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with the N atom attached form a heterocycle; and
$R_4$ represents hydrogen, alkyl, aryl, or heteroaryl,
are useful in the control of arthropods, plant nematode, helminth or protozoan pests. In particular, 5-amino-3-cyano-1-(2,6-dichloro-4-trifluoromethylphenyl)-4-trifluoromethyl sulphinyl pyrazole is an important insecticide and has been known since 1987.

In particular, EP 0295117 describes the preparation of 5-amino-3-cyano-1-(2,6-dichloro-4-trifluoromethylphenyl)-4-trifluoromethyl sulphinyl pyrazole by the oxidation of 5-amino-3-cyano-1-(2,6-dichloro-4-trifluoromethylphenyl)-4-trifluoromethylthiopyrazole with 3-chloroperbenoic acid under high temperature.

Processes for the manufacture of N-substituted pyrazole derivatives having the general formula I are known. For example, EP 0295117 discloses a wide range of ways of preparing N-substituted pyrazole derivatives provides details of thirteen different process schemes for preparing a range of N-substituted pyrazole derivatives.

The use of trifluoroacetic acid and hydrogen peroxide (forming trifluoroperacetic acid in situ) for the oxidation of sulphides to sulphoxides is known. However, the sulphides are difficult to remove from the sulphoxides. The commercial process for the manufacture of N-substituted pyrazole derivatives of general formula I uses corrosive and expensive chemicals such as trifluoroacetic acid (TFA).

WO 01/30760 discloses a process for the preparing of certain N-substituted sulphinyl pyrazole derivatives from the corresponding thio pyrazole compound by oxidation. The reaction is carried out in the presence of trifluoroperacetic acid. The triflouroperacetic acid may be generated in situ by the reaction of trifluoroacetic acid (TFA) with hydrogen peroxide. WO 01/30760 addresses the problem of the highly corrosive nature of the reaction mixture by including a corrosion inhibiting compound, in particular boric acid. This process gives excellent results in terms of both selectivity and yield in preparing 4-trifluoromethylsulphinylpyrazole derivatives. However, this process involves the formation of very corrosive components, for example leading to corrosion of the glass linings of industrial reaction vessels due to the formation of hydrogen fluoride (HF) when used on a large scale. Although addition of a corrosion inhibiting compound, such as boric acid, to the reaction mixture inhibits the corrosion process and reduces the speed of corrosion, there remain severe corrosion problems to the equipment used. In addition, the use of TFA as a reagent makes the commercial operation of the process extremely difficult and expensive.

More recently, U.S. Pat. No. 7,777,052 discloses a process for the preparation of certain N-substituted sulphinyl pyrazoles from the corresponding thio pyrazole compound in a medium comprising at least one oxidizing agent and trichloroacetic acid and/or the reaction product of the oxidizing agent and trichloroacetic acid, together with at least one melting point depressant. Hydrogen peroxide is indicated to be a preferred oxidizing agent for use in combination with trichloroacetic acid. The melting point depressant is required, as trichloroacetic acid is solid under the conditions of oxidation. It would be advantageous if the need to use trichloroacetic acid and the required melting point depressant could be avoided.

Accordingly, there is a need for an improved process for the preparation of N-substituted pyrazole derivatives of the general formula I.

DESCRIPTION OF THE INVENTION

In particular, it would be advantageous if an improved process to prepare N-substituted pyrazole derivatives, such as N-phenyl pyrazole derivatives, in particular 5-amino-3-cyano-1-(2,6-dichloro-4-trifluoromethylphenyl)-4-trifluoromethyl sulphinyl pyrazoles, could be provided without need to employ the corrosive and expensive solvent TFA.

The present invention seeks to provide an improved, for example more economical, process for the preparation of phenyl pyrazole derivatives, in particular 5-amino-3-cyano-1-(2,6-dichloro-4-trifluoromethylphenyl)-4-trifluoromethyl sulphinyl pyrazoles.

In a first aspect, the present invention provides a process for the preparation of a compound of the general formula I:

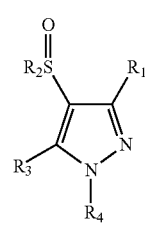

(I)

wherein,
$R_1$ represents hydrogen, cyano, nitro, halogen, or acyl;
$R_2$ represents alkyl, alkenyl, alkynyl, halogen substituted alkyl, halogen substituted alkenyl, or halogen substituted alkynyl;

$R_3$ represents hydrogen or $NR_6R_7$, wherein $R_6$ and $R_7$ each independently represents hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with the N atom attached form a heterocycle; and $R_4$ represents hydrogen, alkyl, aryl, or heteroaryl;

said process comprising the step of oxidizing a compound of general formula II:

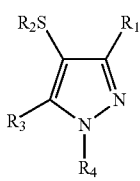

with an oxidant in the absence of trifluoroperacetic acid.

It has been found that compounds of general formula I, in particular those compounds of interest as having pesticidal activity, can be prepared in high yield by the oxidation of compounds of the general formula II, but without the need to rely on the use of TFA or its derivatives, as used extensively in the known prior art processes. The oxidant employed in the process of the present invention to avoid the need to use or form trifluoroperacetic acid may be selected, for example, from quinones, such as benzoquinone, peroxides such as hydrogen peroxide, hypohalites such as sodium hypochlorite, or an alkali metal hydroxide such as sodium hydroxide, preferably the oxidant is hydrogen peroxide. In particular, it has been found that the oxidation of compounds of general formula II may be effected using hydrogen peroxide as the sole oxidizing agent, that is without a further oxidizing agent being added to the process or generated in situ by the action of the hydrogen peroxide.

Accordingly, in another aspect, the present invention provides a process for the preparation of a compound of general formula I:

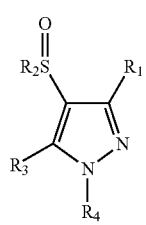

wherein, $R_1$ represents hydrogen, cyano, nitro, halogen, or acyl;

$R_2$ represents alkyl, alkenyl, alkynyl, halogen substituted alkyl, halogen substituted alkenyl, or halogen substituted alkynyl;

$R_3$ represents hydrogen or $NR_6R_7$, wherein $R_6$ and $R_7$ each independently represents hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with the N atom attached form a heterocycle; and $R_4$ represents hydrogen, alkyl, aryl, or heteroaryl;

said process comprising the step of oxidizing a compound of general formula II:

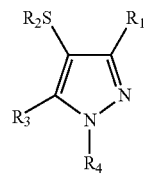

with hydrogen peroxide as the sole oxidant.

As used herein, alkyl groups preferably have from 1 to 20, more preferably from 1 to 10, still more preferably from 1 to 6 carbon atoms. Alkenyl and aklynyl groups preferably have from 2 to 20, more preferably from 2 to 10, still more preferably from 2 to 6 carbon atoms. Alkyl, alkenyl and alkynyl groups may be straight chain or branched. Each may be optionally substituted. Acyl groups may contain from 1 to 20, more preferably from 1 to 10, still more preferably from 1 to 6 carbon atoms, with $C_1$ to $C_4$ acyl groups being especially preferred. Heteroaryl groups may comprise one or more N, S or O atoms. Preferably the aryl group is phenyl. Aryl and heteroaryl groups may bear one or more substituents. Suitable substituents for the optionally substituted groups include halogen, alkyl and alkoxy groups. Halogen is particular preferred substituent.

The compounds of general formula I are N-substituted sulphinyl pyrazoles. R1 in the compounds of formula I may be hydrogen, cyano, nitro, halogen, or acyl. Preferred compounds of general formula I are those in which $R_1$ is cyano.

$R_2$ in the compounds of general formula I represents alkyl, alkenyl, alkynyl, halogen substituted alkyl, halogen substituted alkenyl, or halogen substituted alkynyl. Preferred compounds are those in which $R_2$ is $C_1$-$C_4$ alkyl, $C_2$-$C_4$ alkenyl, $C_2$-$C_4$ alkynyl, $C_1$-$C_4$ halogen substituted alkyl, $C_2$-$C_4$ halogen substituted alkenyl, or $C_2$-$C_4$ halogen substituted alkynyl, more preferably halogen substituted alkyl groups. Particularly preferred compounds are those in which $R_2$ is a halogen substituted methyl group, in particular trifluoromethyl.

$R_3$ in the compounds of general formula I represents hydrogen or $NR_6R_7$, wherein $R_6$ and $R_7$ each independently represents hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with the N atom attached form a heterocycle. Preferred compounds are those in which $R_3$ is the group $NR_6R_7$ in which $R_6$ and $R_7$ each independently represent hydrogen or $C_1$-$C_4$ alkyl. Particularly preferred compounds are those in which $R_3$ is $NH_2$.

$R_4$ in the compounds of general formula I represents hydrogen, or an alkyl, aryl, or heteroaryl moiety. Preferably, $R_4$ is an aryl group, more preferably an optionally substituted phenyl moiety.

In some preferred embodiments, the compound of general formula I is a compound in which $R_4$ is a substituted phenyl group, that is a compound of formula IV:

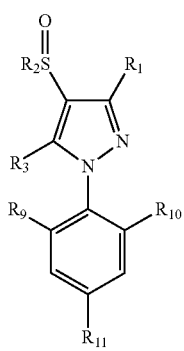

(IV)

wherein $R_1$, $R_2$ and $R_3$ are as hereinbefore described;

$R_9$, $R_{10}$ each independently represent halogen; and $R_{11}$ represents alkyl, alkenyl, alkynyl, halogen substituted alkyl, halogen substituted alkenyl, or halogen substituted alkynyl.

In the compounds of formula IV, $R_9$ and $R_{10}$ are preferably the same. Most preferably, $R_9$ and $R_{10}$ represent chlorine.

$R_{11}$ in the compounds of formula IV preferably represents $C_1$-$C_6$ alkyl, $C_2$-$C_6$ alkenyl, $C_2$-$C_6$ alkynyl, $C_1$-$C_6$ halogen substituted alkyl, $C_2$-$C_6$ halogen substituted alkenyl, or $C_2$-$C_6$ halogen substituted alkynyl. In a first group of preferred compounds, $R_{11}$ represents a halogen substituted alkyl group. Particularly preferred compounds are those in which $R_{11}$ is a halogen substituted methyl group, in particular trifluoromethyl. In a second group of preferred compounds, $R_{11}$ represents a $C_1$-$C_6$ alkyl group, more preferably a $C_1$-$C_4$ alkyl group.

It follows that, in some preferred embodiments, the compound of general formula II is a compound of formula V:

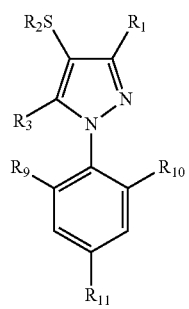

(V)

wherein, $R_1$, $R_2$, $R_3$, $R_9$, $R_{10}$ and $R_{11}$ are as described hereinbefore.

As noted above, the process of the present invention is conducted without the presence or formation of trifluoroacetic acid (TFA). Oxidants for use in the process of the present invention may be selected from quinones such as benzoquinone, peroxides such as hydrogen peroxide, hypohalites such as sodium hypochlorite, or an alkali metal hydroxide such as sodium hydroxide. Preferably the oxidant is hydrogen peroxide. More particularly, in a preferred embodiment of the process of the present invention is carried out in a medium comprising only one oxidizing agent, that is hydrogen peroxide. Hydrogen peroxide may be used in the form of a concentrated aqueous solution, such as those that are available commercially.

Oxidation of compounds of the type of general formula II entails several difficulties, for example that the molecule has to be stable under the conditions of oxidation, the oxidation should proceed to the desired level without leaving significant starting materials unreacted and the oxidation should not produce an excessive level of sulfonyl derivative. Accordingly, the reaction conditions should be selected to address these issues.

The process of the present invention may be carried out at any suitable temperature to effect oxidation of the compounds of general formula II to the compounds of general formula I in sufficiently high yields. Advantageously, it has been found that the process may be effected at a lower temperature than the prior art processes, while still achieving acceptable yields for application on a commercial scale. The temperature for the reaction is chosen so as to give reasonable kinetics for oxidation without decomposing the product. Accordingly, the process may be carried out at a temperature in the range of up to 50° C., preferably up to 20° C., more preferably up to 10° C., still more preferably up to 8° C. The process may be operated at a temperature of from 0° C., more preferably at least 2° C., still more preferably at least 5° C. A temperature in the range of from 0 to 10° C., more preferably 5 to 8° C. is particularly preferred.

The process may be carried out at any suitable pressure, with atmospheric pressure being preferred.

Overall, the invention makes the commercial manufacture of phenyl pyrazole derivatives such as the important insecticide 5-amino-3-cyano-1-(2,6-dichloro-4-trifluoromethylphenyl)-4-trifluoromethyl sulphinyl pyrazole, more process friendly and economically viable. Particularly, the present invention provides a convenient, simple and safe method for preparing 5-amino-3-cyano-1-(2,6-dichloro-4-trifluoromethylphenyl)-4-trifluoromethyl sulphinyl pyrazole using chemicals which do not corrode the equipment used. Further, as noted, the method may be carried out at low pressures (such as atmospheric pressure) and temperatures.

The oxidation reaction is preferably carried out in a suitable solvent, in particular one or more organic solvents. A particularly preferred solvent is ethylene dichloride. Other suitable solvents include tetrahydrofuran, alcohols, such as ethanol and methanol, water, halogen substituted alkanes, such as dichloromethane and trichloromethane, and nitriles, such as acetonitrile.

Surprisingly, contrary to the teachings in the prior art, it has been found that compounds of general formula II may be converted by oxidation into compounds of general formula I, in the absence of other commonly used components, in particular trifluoroperacetic acid. In particular, it has been found that hydrogen peroxide is an oxidant able to achieve the conversion of compounds of general formula II into compounds of general formula I when used as the sole oxidizing agent.

The quantity of the oxidizing agent used is sufficient to effect optimal conversion of the compound of general formula II to the compound of general Formula I without producing significant amounts of the by-product sulphonyl derivative. The oxidant may be employed in a ratio of mole of oxidant per mole of compound of general formula II of from 0.1 to 10, preferably from 0.5 to 5, more preferably from 1.1 to 1.7. For hydrogen peroxide as the oxidizing agent, this is preferably in the range of from 1.01 to 5.0 mole per mole of the compound of general formula II, more preferably from 1.05 to 3.0, still more preferably from 1.1 to 1.7 mole, per mole of the compound of formula II.

Hydrogen peroxide may be used at any suitable concentration in the aqueous solution starting material. The preferred concentration of hydrogen peroxide used is 30% by weight as an aqueous solution due to the commercial availability of such solutions. Concentrations outside this range can also be used with suitable adjustments to the water concentration.

The oxidation of compounds of the general formula II to compounds of general formula I may be carried out in the presence of one or more catalysts, for example a catalyst comprising an organic acid, such as trifluoroacetic acid or acetic acid, an inorganic acid, such as hydrochloric acid, a metal sulfonate, such as scandium tris(trifluoromethanesulfonate), a metal tungstate, such as sodium tungstate, or mixtures thereof, such as a mixture of sodium tungstate and hydrochloric acid.

According to one aspect of the invention, there is provided a process for preparation of a compound of general formula I, which comprises step B of reacting an oxidant with a compound of general formula II in a medium comprising substantially no trifluoroperacetic acid to produce a compound of formula I, according to the reaction scheme below:

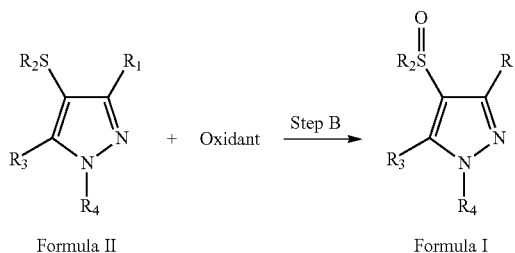

Formula II            Formula I

The oxidant is most preferably hydrogen peroxide.

According to another aspect of the invention, there is provided a process for preparation of a compound of general formula I, which comprises step A of reacting $CF_3SCl$ with a compound of general formula III to produce a compound of general formula II, and step B of reacting an oxidant with the compound of general formula II in a medium comprising substantially no trifluoroperacetic acid to produce a compound of general formula I, according to the reaction scheme below:

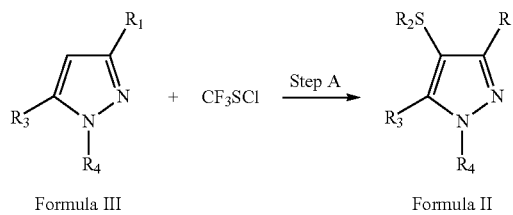

Formula III            Formula II

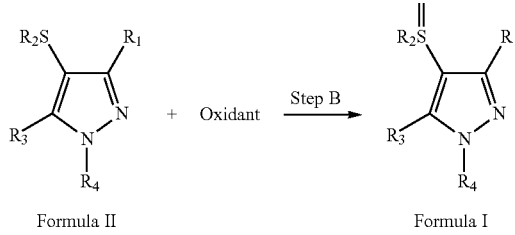

Formula II            Formula I

In the compound of general formula III, $R_1$, $R_2$ and $R_3$ are as hereinbefore defined.

According to another aspect of the invention, there is also provided a process for the preparation of a compound of general formula II, which comprises step A:

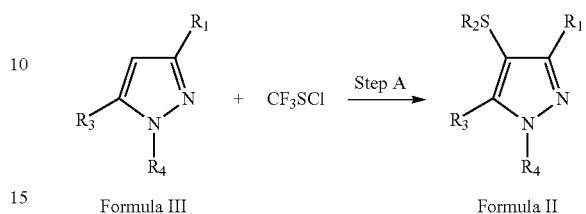

Formula III            Formula II

According to another aspect of the invention, there is provided a process for the preparation of a compound of formula IV, which comprises step B of reacting an oxidant with a compound of formula V in a medium comprising substantially no trifluoroperacetic acid to produce a compound of formula IV, according to the reaction scheme below:

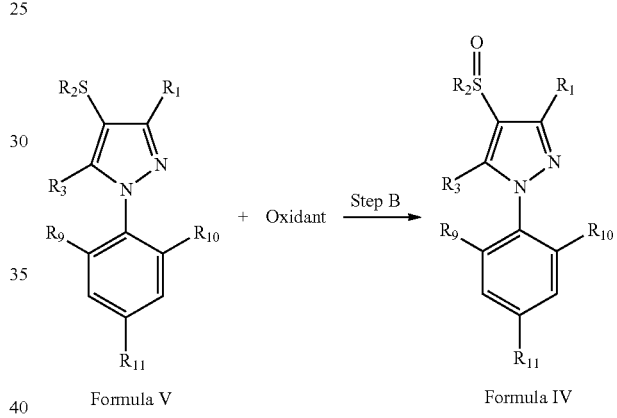

Formula V            Formula IV

The oxidant is most preferably hydrogen peroxide.

According to another aspect of the invention, there is provided a process for preparation of a compound of formula IV, which comprises step A of reacting $CF_3SCl$ with a compound of formula VI to produce a compound of formula V, and step B of reacting an oxidant with a compound of formula V in a medium comprising substantially no trifluoroperacetic acid to produce a compound of formula IV, according to the reaction scheme below:

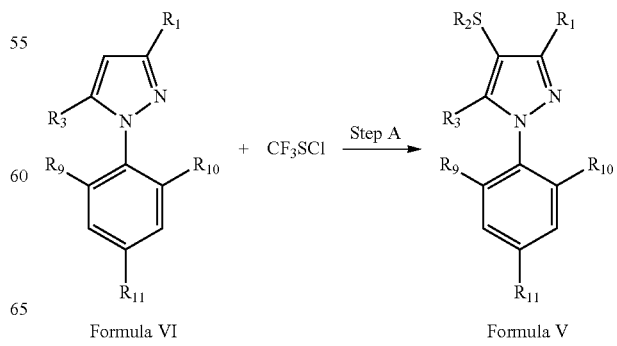

Formula VI            Formula V

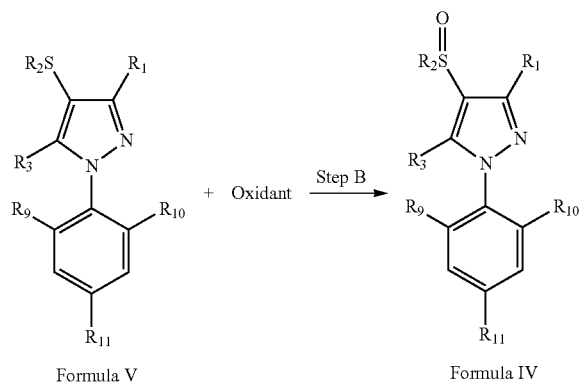

Formula V          Formula IV

In the compound of general formula VI, $R_1$, $R_2$, $R_3$, $R_9$, $R_{10}$ and $R_{11}$ are as hereinbefore defined.

According to another aspect of the invention, there is also provided a process for preparation of a compound of formula V, which comprises step A:

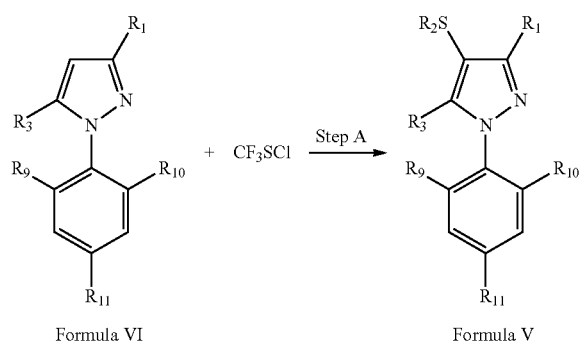

Formula VI          Formula V

As noted above the oxidant in the process of the present invention may be selected from quinones such as benzoquinone, peroxides such as hydrogen peroxide, hypohalites such as sodium hypochlorite, or an alkali metal hydroxide such as sodium hydroxide, preferably the oxidant is hydrogen peroxide. In some preferred embodiments, hydrogen peroxide is used as the exclusive oxidant.

Preferably, the process steps of the present invention is carried out at a temperature in the ranges described above. In particular, of from 0 to 50° C., more preferably in the range of 0 to 10° C., most preferably in the range 5 to 8° C. Steps A and B may be carried out at the same or different temperatures. Thus, in one embodiment, step A of the process is carried out at a temperature in the range of 0 to 50° C., preferably in the range of 10 to 30° C., more preferably in the range 15-25° C. In another embodiment, step B of the process is carried out at a temperature in the range of 0 to 50° C., preferably in the range of 0 to 10° C., more preferably in the range 5 to 8° C.

As noted, the process steps of the present invention may be carried out at a lower pressure, preferably atmospheric pressure. Again, steps A and B may be conducted at the same or different pressures. In one embodiment, step A of the process is carried out at atmospheric pressure. In another embodiment, step B of the process is carried out at atmospheric pressure.

Preferably, the process steps of the present invention is carried out in the medium comprising organic solvent. The solvent used in steps A and B may be the same or different. In one embodiment, step A of the process is carried out in the medium comprising an organic solvent, preferably dichloromethane. In another embodiment, step B of the process is carried out in the medium comprising an organic solvent, preferably ethylene dichloride.

According to an aspect of the invention, the process is carried out in a medium comprising substantially no trifluoroperacetic acid. In some embodiments, step A of the process of the present invention is carried out in a medium comprising substantially no trifluoroperacetic acid. In other embodiments, step B of the process of the present invention is carried out in a medium comprising substantially no trifluoroperacetic acid.

According to another aspect of the invention, the process is carried out without formation of HF. In some embodiments, step A of the process of the present invention is carried out without formation of HF. In other embodiments, step B of the process of the present invention is carried out without formation of HF.

As noted above, the process step B may be carried out with the molar ratio of the oxidant (such as hydrogen peroxide) to the compound of general formula II of from 0.1 to 10, preferably from 0.5 to 5, more preferably from 1.1 to 1.7.

In the process, step A may carried out with the molar ratio of the compound of general formula III to $CF_3SCl$ from 0.1 to 10, preferably 0.5 to 5, more preferably 0.8 to 1.5.

As noted above, step B of the process scheme may be conducted using one or more catalysts. Step A of the process scheme may employ a catalyst. However, step A of the process may conveniently be conducted without the use of a catalyst for the reaction.

Embodiments of the present invention will now be described by way of the following examples for illustrative purposes only.

Example 1

Preparation of 5-amino-3-cyano-1-(2,6-dichloro-4-trifluoromethylphenyl)-4-trifluoromethylthio pyrazole 360 kg (1.12 kmol) 5-Amino-1-[2,6-dichloro-4-(trifluoromethyl)phenyl]-1H-pyrazole-3-carbonitrile diluted with 300 kg dichloromethane are added to 1000 L multiple stirrer gas/liquid (MSGL) reactor and the whole mass is stirred along with steady cooling until the mixture temperature is below 10° C. Thereafter, 155 kg (1.14 k mol) trifluoromethanesulphenyl chloride gas is introduced into the reaction mass over a period of 12 hours at a temperature of from 18 to 20° C. with the feed rate controlled using a weighing scale. The excess unreacted trifluoromethanesulphenyl chloride gas is scrubbed and absorbed using chilled dichloromethane, followed by scrubbing with sodium hydroxide solution.

After the reaction is completed, as indicated by disappearance of the pyrazole intermediate using HPLC analysis, the reaction mass was allowed to warm slowly up to room temperature with stirring for an additional 2 hours to ensure completion of the reaction and removal of excess trifluromethanesulphenyl chloride.

The resulting reaction mass is washed with 2×200 liter DM water with stirring for 40 to 60 minutes for each washing, and finally allowed to settle for 30 to 45 minutes until a clear separation of two layers is achieved. Thereafter, the lower water layer is separated and the remaining organic layer is washed again with 200 liter 5% aqueous solution of sodium hydroxide. This washing is repeated if required to obtain a pH of 7.00. Thereafter, the organic liquid is dried by passing & percolating over anhydrous calcium chloride.

Thereafter, the solvent dichloromethane is distilled off and the residue is slowly cooled to 0° C. and maintained for 3 to 5 hours with slow stirring to complete precipitation. The precipitated mass is filtered and centrifuged to isolate a wet cake, which is repeatedly washed with lots of 20.0 kg dichloromethane. The resulting cake is dried for 6 to 8 hours at 100 to 105° C. in a vacuum rotary evaporator to yield 300 to 310.00 kg of white/brown solid. This intermediates product is 5-amino-1-(2,6-dichloro-4-(trifluoromethyl)phenyl)-4-(trifluorormethylthio)-1H-pyrazole-3-carbonitrile, having a melting point of 170-171° C. The yield of this step reaction is approximately 65-68% based upon pyrazole.

The reaction is schematically depicted below.

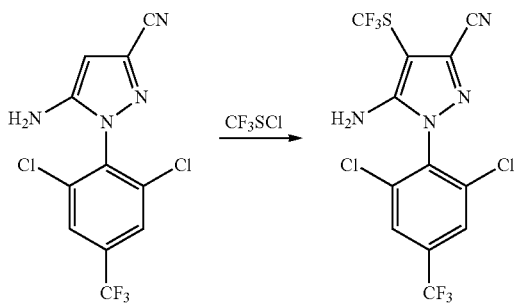

Example 2

Preparation of Crude 5-amino-3-cyano-1-(2,6-dichloro-4-trifluoromethylphenyl)-4-trifluoromethyl sulphinyl pyrazole 1250 kg ethylene dichloride and 300 kg (0.71 kmol) 5-amino-1-(2,6-dichloro-4-(trifluoromethyl)phenyl)-4-(trifluorormethylthio)-1H-pyrazole-3-carbonitrile are added to a 2000 L MSGL reactor and the mass is stirred until complete dissolution of the solid intermediate occurs and results in a clear solution. The resultant solution is cooled to a temperature of from 2 to 5° C. and 20 kg of a catalyst mixture consisting of 10 kg of sodium tungstate and 10 kg of hydrochloric acid (30% by weight) is added in small lots. The colour of the reaction mass is a red/yellow transparent solution after complete mixing of the catalyst.

Thereafter, 150 kg 30% hydrogen peroxide is diluted and added over a period of 10 to 12 hours, while maintaining the reaction temperature in the range of 5 to 8° C. After the addition of the hydrogen peroxide solution, the reaction mass is further maintained at the same temperature under stifling for an additional 10 hours. Excess hydrogen peroxide is then neutralized by washing with a dilute solution of 5% (aq) sodium bicarbonate. The solution is stirred at 1 to 2° C. until precipitation is completed and the mass is filtered to isolate a wet cake, which is repeatedly washed with ethylene chloride to remove unreacted organic compounds and other impurities. The cake is dried for 6 to 8 hours at 100 to 105° C. to remove any moisture and low volatility compounds to yield 285 to 290 kg of crude 5-amino-3-cyano-1-(2,6-dichloro-4-trifluoromethylphenyl)-4-trifluoromethyl sulphinyl pyrazoles having approximate purity of 90 to 92.50%. The yield of this step reaction is averaged between 84.50 to 86.50%.

The chemical reaction is depicted below.

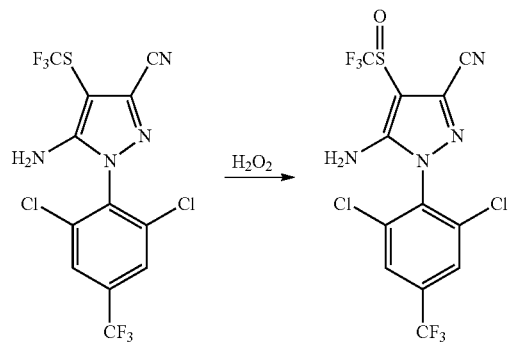

Example 3

Purification of Crude 5-amino-3-cyano-1-(2,6-dichloro-4-trifluoromethylphenyl)-4-trifluoromethyl sulphinyl pyrazoles Technical 570 Kg of crude 5-amino-3-cyano-1-(2,6-dichloro-4-trifluoromethylphenyl)-4-trifluoromethyl sulphinyl pyrazole is added to a mixture of 640 kg dichloromethane and 160 kg butyl ethanoate in a 1500 Liter stainless steel reactor, fitted with a 30.0 m² stainless steel heat exchanger. The mixture is stirred and slowly allowed to heat up to 40 to 50° C. The mixture is held at this temperature for 2 to 3 hours and then the mass is cooled to room temperature. The precipitated mass is filtered by centrifuging along with repeated washing with 50 kg fractions of dichloromethane. The washed cake is dried for a period of 4 to 6 hours in a rotary vacuum drier to give 495 to 505 Kg of pure 5-amino-3-cyano-1-(2,6-dichloro-4-trifluoromethylphenyl)-4-trifluoromethyl sulphinyl pyrazole TG having a purity ranging from 97.00 to 98.50% as confirmed by HPLC analysis.

The invention claimed is:
1. A process for the preparation of a compound of formula I:

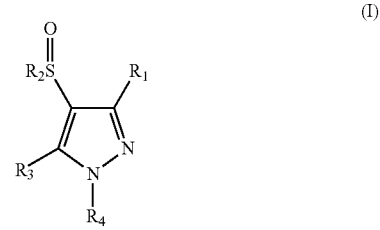

wherein,
$R_1$ represents hydrogen, cyano, nitro, halogen, or acyl;
$R_2$ represents alkyl, alkenyl, alkynyl, halogen substituted alkyl, halogen substituted alkenyl, or halogen substituted alkynyl;
$R_3$ represents hydrogen or $NR_6R_7$ wherein $R_6$ and $R_7$ each independently represent hydrogen, alkyl, alkenylalkyl, alkynylalkyl, formyl, optionally halogen substituted alkanoyl, optionally halogen substituted alkoxycarbonyl, or alkoxymethyleneamino, halogen, or $R_6$ and $R_7$ together with the N atom attached form a heterocycle; and
$R_4$ represents hydrogen, alkyl, aryl, or heteroaryl;

said process comprising oxidizing a compound of formula II:

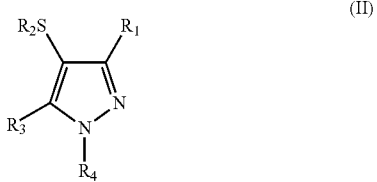

with an oxidant in the absence of trifluoroperacetic acid and in the presence of a catalyst comprising sodium tungstate and hydrochloric acid.

2. The process according to claim 1, wherein $R_1$ is cyano.

3. The process according to claim 1, wherein $R_2$ is $C_1$ to $C_4$ alkyl, $C_2$ to $C_4$ alkenyl, $C_2$ to $C_4$ alkynyl, $C_1$ to $C_4$ halogen substituted alkyl, $C_2$ to $C_4$ halogen substituted alkenyl, or $C_2$ to $C_4$ halogen substituted alkynyl.

4. The process according to claim 3, wherein $R_2$ is trifluoromethyl.

5. The process according to claim 1, wherein $R_3$ is $NR_6R_7$ and $R_6$ and $R_7$ each independently represent hydrogen or $C_1$ to $C_4$ alkyl.

6. The process according to claim 1, wherein $R_4$ is an optionally substituted phenyl moiety.

7. The process according to claim 1, wherein the compound of formula I is a compound of formula IV:

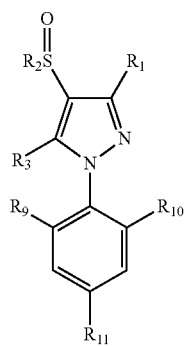

wherein $R_9$, $R_{10}$ each independently represent halogen; and
$R_{11}$ represents alkyl, alkenyl, alkynyl, halogen substituted alkyl, halogen substituted alkenyl, or halogen substituted alkynyl;
and the compound of formula II is a compound of formula V:

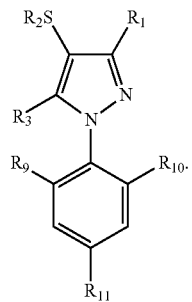

8. The process according to claim 7, wherein $R_9$ and $R_{10}$ are both chlorine.

9. The process according to claim 7, wherein $R_{11}$ is trifluoromethyl or $C_1$ to $C_6$ alkyl.

10. The process according to claim 7, wherein the compound of formula IV is 5-amino-3-cyano-1-(2,6-dichloro-4-trifluoromethylphenyl)-4-trifluoromethyl sulphinyl pyrazole.

11. The process according to claim 1, wherein the process is carried out at a temperature in the range of 0 to 10° C.

12. The process according to claim 11, wherein the temperature is in the range of 5 to 8° C.

13. The process according to claim 1, wherein the oxidation is carried out in the presence of an organic solvent.

14. The process according to claim 13, wherein the organic solvent comprises ethylene dichloride.

15. The process according to claim 1, wherein the oxidant comprises a quinone, a peroxide, a hypohalite, or an alkali metal hydroxide.

16. The process according to claim 15, wherein the oxidant comprises hydrogen peroxide.

17. The process according to claim 16, wherein hydrogen peroxide is the sole oxidant.

18. The process according to claim 1, wherein the molar ratio of oxidant to the compound of general formula II is from 0.1 to 10.

19. The process according to claim 18, wherein the molar ratio of oxidant to the compound of general formula II is from 0.5 to 5.

20. The process according to claim 19, wherein the molar ratio of oxidant to the compound of general formula II is from 1.1 to 1.7.

21. A process for preparation of a compound of formula IV according to claim 7, which further comprises reacting $CF_3SCl$ with a compound of formula VI to produce a compound of formula V according to step A below; and the oxidizing comprises reacting an oxidant with a compound of formula V in a medium comprising substantially no trifluoroperacetic acid and in the presence of a catalyst comprising sodium tungstate and hydrochloric acid to produce a compound of formula IV, according to step B of the reaction scheme below:

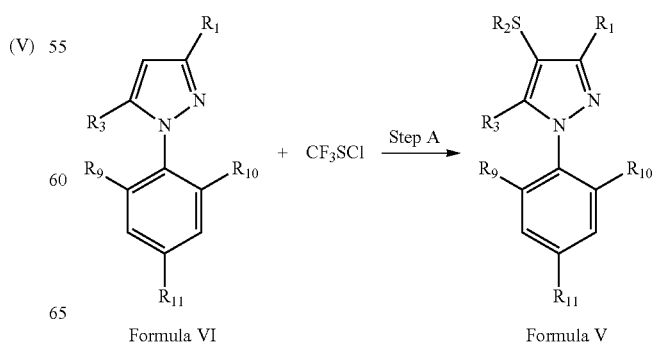

-continued

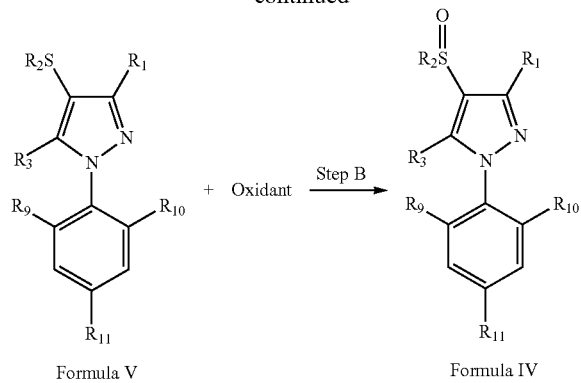

Formula V → Formula IV

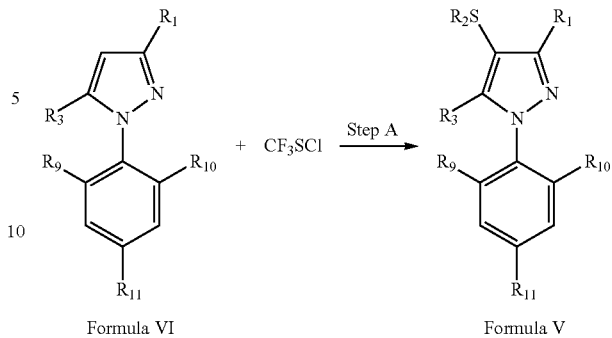

Formula VI → Formula V wherein,
R₁ represents hydrogen, cyano, nitro, halogen, or acyl;
R₂ represents trifluoromethyl;
R₃ represents hydrogen or NR₆R₇ wherein R₆ and R₇ each independently represent hydrogen, alkyl, alkenylalkyl, alkynylalkyl, formyl, optionally halogen substituted alkanoyl, optionally halogen substituted alkoxycarbonyl, or alkoxymethyleneamino, halogen, or R₆ and R₇ together with the N atom attached form a heterocycle;
R₉, R₁₀ each independently represent a halogen; and
R₁₁ represents alkyl, alkenyl, alkynyl, halogen substituted alkyl, halogen substituted alkenyl, or halogen substituted alkynyl.

22. A process for preparation of a compound of formula V, which comprises step A:

wherein,
R₁ represents hydrogen, cyano, nitro, halogen, or acyl;
R₂ represents trifluoromethyl;
R₃ represents hydrogen or NR₆R₇ wherein R₆ and R₇ each independently represent hydrogen, alkyl, alkenylalkyl, alkynylalkyl, formyl, optionally halogen substituted alkanoyl, optionally halogen substituted alkoxycarbonyl, or alkoxymethyleneamino, halogen, or R₆ and R₇ together with the N atom attached form a heterocycle;
R₉, R₁₀ each independently represent a halogen; and
R₁₁ represents alkyl, alkenyl, alkynyl, halogen substituted alkyl, halogen substituted alkenyl, or halogen substituted alkynyl.

23. The process according to claim 22, wherein R₁ represents $C_1$-$C_4$ acyl.

* * * * *